United States Patent [19]

Langer et al.

[11] 4,287,131

[45] Sep. 1, 1981

[54] PREPARATION OF METAL ORGANOPOLYPHOSPHATE COORDINATION OF COMPLEXES

[75] Inventors: Horst G. Langer, Wayland; Thomas P. Brady, Holliston, both of Mass.

[73] Assignee: The Dow Chemical Company, Midland, Mich.

[21] Appl. No.: 116,134

[22] Filed: Jan. 28, 1980

[51] Int. Cl.³ .............................................. C07F 5/06
[52] U.S. Cl. ............................ 260/448 R; 260/429 J; 260/429 R; 260/429.3; 260/429.7; 260/439 R; 260/448 AD; 260/980; 260/988
[58] Field of Search .................. 260/988, 980, 448 R, 260/429 R, 439 R, 429.7, 429.3, 429 J

[56] References Cited

U.S. PATENT DOCUMENTS

| | | | |
|---|---|---|---|
| 3,062,858 | 11/1962 | Cramer | 260/933 X |
| 3,150,039 | 9/1964 | Lanham et al. | 260/933 X |
| 3,276,916 | 10/1966 | Wurstner | 260/980 X |
| 3,470,222 | 9/1969 | Jennings | 260/988 X |
| 3,692,881 | 9/1972 | Stanford et al. | 260/980 X |
| 3,960,592 | 6/1976 | Birchall et al. | 260/448 R X |
| 4,104,173 | 8/1978 | Gay et al. | 260/448 R X |
| 4,152,289 | 5/1979 | Griffin | 260/980 X |
| 4,153,066 | 5/1979 | Griffin | 260/980 X |
| 4,153,649 | 5/1979 | Griffin | 260/980 X |
| 4,174,283 | 11/1979 | Griffin | 260/980 X |

*Primary Examiner*—Helen M. S. Sneed
*Attorney, Agent, or Firm*—Douglas N. Deline

[57] ABSTRACT

Metal alkoxides are reacted with phosphorus pentoxide to produce metal organopolyphosphate coordination polymers.

6 Claims, No Drawings

PREPARATION OF METAL ORGANOPOLYPHOSPHATE COORDINATION OF COMPLEXES

BACKGROUND OF THE INVENTION

The invention relates to a process for preparing metal organopolyphosphates which advantageously permits formation of coordination polymers having essentially any desired ratio of metal to phosphorus. The process has been found to allow more rapid production of metal organopolyphosphate coordination complexes than has heretofore been obtainable.

It has been known to react alkanols with phosphorus pentoxide in a slurry with a hydrocarbon solvent in order to produce improved extractants for metal ore values. Such a process is taught in U.S. Pat. No. 2,866,680 and in U.S. Pat. No. 2,947,774.

SUMMARY OF THE INVENTION

According to the present invention, a metal alkoxide is contacted with phosphorus pentoxide in an inert liquid organic medium resulting in the production of an organopolyphosphate coordination complex with the metal compound.

The resulting compounds have been found to be useful as polymer additives, corrosion inhibitors for functional fluids and as fire retardants for cellulosic materials.

DETAILED DESCRIPTION OF THE INVENTION

The metal alkoxides suitable for use according to the invention include well-known metal alkoxides of $C_{1-5}$ alkanols such as potassium ethoxide, potassium tert-butylate, magnesium methylate, magnesium ethylate, calcium methylate, calcium ethylate, aluminum isopropylate, aluminum sec-butylate, titanium tetraisopropoxide, titanium tetra-n-butoxide, etc. Also included are halogenated derivatives of the above alkoxides.

Further metal alkoxides are the metal derivatives of glycol ethers of the formula

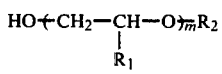

wherein $R_1$ is independently each occurrence hydrogen, methyl or halomethyl; $R_2$ is independently each occurrence $C_{1-4}$ alkyl or phenyl and m is a number from 1 to 5.

Also included are metal alkoxide derivatives of $C_{1-10}$ alkanolamines of the formula $R_3$—N—$(Z)_2$ where $R_3$ is $C_{1-10}$ hydroxyalkyl, and Z is each occurrence hydrogen, $C_{1-3}$ alkyl or hydroxyalkyl.

The latter compounds may be prepared by alkoxide exchange between commercially available metal alcoholates and the named hydroxyl-containing compounds or mixtures thereof. The reaction product includes a more volatile alkanol, for example, methanol, ethanol, propanol, depending on the metal alcoholate employed. This volatile reaction product may be removed from the reaction by vacuum or other means thus driving the reaction towards the production of the metal alkoxide. Some metal alkoxides may also be produced by direct reaction of a sufficiently reactive metal with the desired hydroxyl-containing compound or a mixture thereof. Suitable metals known to form stable alkoxides are aluminum, beryllium, magnesium, zinc, barium, gallium, indium, thallium, iron, tin and titanium.

The invented process comprises the reaction of the metal alkoxide with phosphorus pentoxide by contacting the metal alkoxide with phosphorus pentoxide preferably in an inert organic liquid. Preferably the temperature is maintained at less than about 150° C. and the liquid organic medium is $CH_2Cl_2$. In order to produce the preferred diphosphate and polyphosphate coordination complexes, the metal alkoxide is reacted with an excess of phosphorus pentoxide. Preferably the reactants are combined as previously explained until an alkoxy-functionality to phosphorus ratio of from about 0.5:1 to about 1:1 is obtained. The produce may be easily recovered by solvent evaporation or other standard means and neutralized by ammonia or amine compounds either before or after recovery.

It is also possible in the operation of the present invention to combine the two previously described steps of forming the metal alkoxide and then reacting it with $P_2O_5$. Accordingly, the metal and hydroxyl-containing compound may be added slowly in small aliquots to phosphorus pentoxide slurried in an inert organic solvent. By maintaining an excess of phosphorus pentoxide in the early stages of the reaction the detrimental hydrolysis reaction yielding monophosphate esters may be avoided.

SPECIFIC EMBODIMENTS

The following examples are included as further illustrative and are not to be construed as limiting.

EXAMPLE 1

Aluminum isopropoxide (20.4 g, 0.1 mole) was added to a solution of butoxyethanol (47.2 g, 0.4 mole) in 200 ml $CH_2Cl_2$. The solution was stripped of solvent on a rotary evaporator then heated in vacuo over steam to remove isopropanol released by the alkoxide exchange. A white waxy solid having a weight of 50.5 grams remained. The product, thought to be an aluminum coordination complex, was found to contain aluminum and the radical of butoxyethanol and had an empirical formula $HAl(OCH_2CH_2OBu)_4$.

EXAMPLE 2

The produced produced in Example 2 was dissolved in 200 ml $CH_2Cl_2$ and slowly added by means of a dropping funnel to a stirred slurry of $P_2O_5$ (28.5 g, 0.2 mole) in 200 ml $CH_2Cl_2$.

The reaction mixture increased in viscosity and the solvent refluxed from the exothermic reaction. Upon complete addition of the aluminum compound a clear homogeneous gel was obtained.

EXAMPLE 3

The viscosity of the product obtained in example 2 is greatly reduced by neutralization of the acid functionality with ammonia. Accordingly, dry $NH_3$ gas was bubbled into the solution produced in Example 2 until the gel broke. The product may be recovered as a white, solid precipitate by shaking with excess water.

EXAMPLE 4

Aluminum tri(2-n-butoxyethoxide) was prepared by incremental addition of pure aluminum turnings to anhydrous 2-n-butoxyethanol. Accordingly, to a 3-liter flask fitted with condenser, stirrer and inlet for dry $N_2$ 2-n-butoxyethanol (944 g, 8.0 moles) was added and heated to a reflux temperature of approximately 160° C. Approximately 5 grams of aluminum turnings were added. Evolution of $H_2$ gas is observed after 2 to 10 hours signifying the reaction has begun. A catalytically effective quantity of $HAl(OCH_2CH_2OBu)_4$ (prepared in Example 1) added to the reaction flask substantially shortens the induction period required.

Once the reaction began additional portions of aluminum turnings were added every 5 to 10 minutes and the temperature of the reaction was lowered to about 120° C.-130° C. A total of 63 grams, 2.33 moles of aluminum were reacted in this manner to provide a viscous liquid product.

A different alcohol 2,2,2-tri(bromomethyl)-ethanol (432 g, 1.33 moles), dissolved in about 500 ml $CH_2Cl_2$ was then added to the neat aluminum alkoxide to produce an equilibrium mixture of aluminum alkoxides in which 2-butoxyethoxy and 2,2,2-tri(bromomethyl)ethoxy radicals were present in a 6:1 ratio dissolved in $CH_2Cl_2$.

EXAMPLE 5

In a 12-liter glass flask equipped with a stirrer, condenser and dry $N_2$ inlet, $P_2O_5$ (700 g, 4.93 moles, 5 mole percent excess) was slurried with 5 liters of $CH_2Cl_2$. The mixed aluminum alkoxide prepared in Example 4 above dissolved in $CH_2Cl_2$ was slowly added with stirring so as to maintain a gentle reflux. Complete addition of aluminum reactant was obtained over a period of 3–4 hours. The final product after all alkoxide reactant was added was saturated with $NH_3$ to break any viscous gel formed and diluted with $CH_2Cl_2$ to a final volume of about 9 liters (approximately 21 percent of the phosphate complex by weight) for treating of wood panels for fire retardancy.

EXAMPLE 6

Preweighed strips of plywood (douglas fir $\frac{1}{4}''\times 3\frac{1}{2}''\times 24''$) were loaded into a treating chamber and the chamber evacuated to a pressure of 1" mercury for 30 minutes. The solution to be used in treating the strips was added to the evacuated chamber and pressure (200 lb/in$^2$) was applied by adding compressed nitrogen.

The pressure was released and the strips removed. Excess surface solution was wiped off. After drying under ambient conditions the strips were heated to 100° C. for several hours and finally rehumidifed at 50 percent relative humidity and ambient temperature for several days. By comparing the weights of the strips initially and after the treatment and drying procedure, a figure reflecting the percent fire-retardant add-on, known as dry add-on percent, was obtained. Different concentrations of treating solutions can be utilized to produce strips having varying amounts of fire-retardant add-on.

EXAMPLE 7

The treating procedure of Example 6 was used to prepare a number of wooden strips. The solutions used had concentrations of the aluminum complex fire retardant of Example 6 of 21, 16 and 12 percent, respectively, providing dry add-on percent values (calculated according to the procedure of Example 6) of from 20 percent to 8 percent.

Seven such strips selected over the range of dry add-on percent values were ignited in a two-foot tunnel designed to simulate the ASTM E-84, 25-foot (Steiner) tunnel test. Accordingly, flame spread is reported in comparison to that obtained on asbestos hardboard and a red oak hardwood standards to which the igniting flame is adjusted to produce maximum flame spread of 8–9 inches and 24 inches, respectively, after 4 minutes. When so tested the strips produced maximum flame spreads of from 15 to 17 inches to qualify as Class II rated fire retardants.

EXAMPLE 8

A 1-liter three-necked, round bottom flask equipped with a mechanical stirrer, heating mantle, thermometer and condenser was maintained under nitrogen atmosphere. The hydroxyl-containing compound N,N-dimethylethanolamine (203 g, 2.29 moles) was added and the flask heated to boiling, about 135° C.

Aluminum turnings (3 g) were added to the flask. A small amount (approx. 0.5 ml) of $HAl(OCH_2CH_2OBu)_4$ produced in Example 1 was also added as an initiator and the temperature of the flask maintained at reflux. Initiation of the reaction was observed to occur after about three hours upon evolution of hydrogen gas. Small amounts of aluminum (about 0.5 g) were added at intervals when hydrogen evolution ceased over a period of several hours until a total of 20.5 g had been added.

When further reaction with aluminum no longer was observed, a viscous, dark colored material which was found to be soluble in toluene, dichloromethane and methylchloroform remained in the reaction flask. Analysis by nuclear magnetic resonance spectroscopy indicated no residual N,N-dimethylethanolamine remained.

EXAMPLE 9

A portion of the product produced in Example 8 was dissolved in dichloromethane solvent. This solution was then added dropwise to a stirred slurry of $P_2O_5$ in dichloromethane at room temperature under a nitrogen atmosphere. After several hours a reaction began, resulting in the formation of a solid, dark colored reaction product which was sparingly soluble in toluene. Analysis by $^{31}P$ and $^{1}H$ nuclear magnetic resonance spectroscopy confirmed the product's identity as an aluminum-containing complex of the N,N-dimethylaminoethoxy partial ester of polyphosphoric acid.

What is claimed is:

1. A process for preparing metal organopolyphosphate coordination complexes comprising contacting a metal alkoxide selected from the group consisting of the aluminum, beryllium, magnesium, zinc, barium, gallium, indium, thallium, iron, tin and titanium alkoxides of (a) $C_{1-5}$ alkanols or haloalkanols;

(b) glycol ethers of the formula

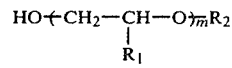

where $R_1$ is independently each occurrence hydrogen, methyl, or halomethyl; $R_2$ is independently $C_{1-4}$ alkyl or phenyl, and n is a number from 1 to 5; and (c) $C_{1-10}$ alkanolamines of the formula $R_3\text{-N-}(Z)_2$ where $R_3$ is $C_{1-10}$ hydroxyalkyl, and Z is each occurrence hydrogen, $C_{1-3}$ alkyl or hydroxyalkyl, with a slurry comprising a mixture of phosphorus pentoxide in an inert liquid organic medium in a ratio of alkoxy-functionality to phosphorus of 0.5:1 to 1:1, at a temperature less than 150° C.

2. The process of claim 1 wherein the metal organopolyphosphate coordination complex is recovered.

3. The process of claim 2 wherein the metal organopolyphosphate coordination complex is recovered by solvent removal.

4. The process of claim 1 wherein the inert liquid organic medium is $CH_2Cl_2$.

5. The process of claim 1 wherein the metal alkoxide is an aluminum alkoxide.

6. The process of claim 5 wherein the metal alkoxide is a metal alkoxide formed by reaction of aluminum triisopropoxide with four equivalents of butoxyethanol.

* * * * *

UNITED STATES PATENT AND TRADEMARK OFFICE
CERTIFICATE OF CORRECTION

PATENT NO. : 4,287,131

DATED : September 1, 1981

INVENTOR(S) : Horst G. Langer and Thomas P. Brady

It is certified that error appears in the above—identified patent and that said Letters Patent is hereby corrected as shown below:

Column 2, line 14, "produce" should read --product--.

Column 2, line 46, "produced" should read --product--.

Column 2, line 46, "Example 2" should read --Example 1--.

Column 3, line 32, "gel" should read --gels--.

Column 3, line 48, "rehumidifed" should read --rehumidified--.

Signed and Sealed this

Twenty-fourth Day of November 1981

[SEAL]

Attest:

Attesting Officer

GERALD J. MOSSINGHOFF

Commissioner of Patents and Trademarks